(12) United States Patent
Feng et al.

(10) Patent No.: US 8,825,178 B2
(45) Date of Patent: Sep. 2, 2014

(54) ELECTRODE LEAD OF PACEMAKER AND PACEMAKER

(75) Inventors: Chen Feng, Beijing (CN); Li Qian, Beijing (CN); Yu-Quan Wang, Beijing (CN); Liang Liu, Beijing (CN); Wen-Mei Zhao, Beijing (CN); Li Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 12 days.

(21) Appl. No.: 13/527,782

(22) Filed: Jun. 20, 2012

(65) Prior Publication Data
US 2013/0110212 A1 May 2, 2013

(30) Foreign Application Priority Data
Oct. 28, 2011 (CN) .......................... 2011 1 0333485

(51) Int. Cl.
*A61N 1/00* (2006.01)
*A61B 5/04* (2006.01)
*B82Y 15/00* (2011.01)
*H01B 1/04* (2006.01)
*H01B 1/02* (2006.01)
*B82Y 30/00* (2011.01)
*A61N 1/05* (2006.01)

(52) U.S. Cl.
CPC .................. *A61N 1/056* (2013.01); *B82Y 15/00* (2013.01); *H01B 1/04* (2013.01); *H01B 1/02* (2013.01); *B82Y 30/00* (2013.01); *A61N 1/057* (2013.01)
USPC ............................... 607/119; 607/5; 600/373

(58) Field of Classification Search
CPC .................................. B82Y 5/00; B82Y 40/00
USPC ......................................... 607/5, 119; 600/373
See application file for complete search history.

(56) References Cited

U.S. PATENT DOCUMENTS

| | | | |
|---|---|---|---|
| 5,713,945 | A | 2/1998 | Fischer et al. |
| 7,493,160 | B2 | 2/2009 | Weber et al. |
| 7,596,415 | B2 | 9/2009 | Brabec et al. |
| 2009/0062895 | A1 | 3/2009 | Stahmann et al. |
| 2009/0194313 | A1 | 8/2009 | Jiang et al. |
| 2009/0255706 | A1 | 10/2009 | Jiang et al. |
| 2010/0147829 | A1 | 6/2010 | Liu et al. |
| 2010/0298895 | A1* | 11/2010 | Ghaffari et al. .................... 607/3 |
| 2011/0301657 | A1* | 12/2011 | Walsh et al. ....................... 607/5 |

FOREIGN PATENT DOCUMENTS

| | | |
|---|---|---|
| TW | 200945372 | 11/2009 |
| TW | 201039670 | 11/2010 |
| TW | I345792 | 7/2011 |

* cited by examiner

*Primary Examiner* — Nicole F Lavert
(74) *Attorney, Agent, or Firm* — Novak Druce Connolly Bove + Quigg LLP

(57) ABSTRACT

An electrode lead of a pacemaker includes a lead wire. The lead wire includes at least one sub-lead wire and an electrode head electrically connected with the lead wire. The sub-lead wire includes a core wire structure and a carbon nanotube composite structure wound around the core wire structure. The pacemaker includes a pulse generator and the electrode lead electrically connected to the pulse generator.

17 Claims, 10 Drawing Sheets

ELECTRODE LEAD OF PACEMAKER AND PACEMAKER

This application claims all benefits accruing under 35 U.S.C. §119 from China Patent Application No. 201110333485.2, filed on Oct. 28, 2011, in the China Intellectual Property Office, the contents of which are hereby incorporated by reference. This application is related to common-assigned applications entitled, "METHOD FOR MAKING PACEMAKER ELECTRODE LEAD," filed on Jun. 20, 2012, and application Ser. No. 13/527,780; "ELECTRODE LEAD OF PACEMAKER AND PACEMAKER USING THE SAME" filed on Jun. 20, 2012, and application Ser. No. 13/527,784; "PACEMAKERS AND PACEMAKER LEADS" filed on Jun. 20, 2012, and application Ser. No. 13/527,792; "PACEMAKERS AND PACEMAKER LEADS" filed on Jun. 20, 2012, and application Ser. No. 13/527,801; "ELECTRODE LEAD OF PACEMAKER AND PACEMAKER USING THE SAME" filed on Jun. 20, 2012, and application Ser. No. 13/527,808; "ELECTRODE LEAD OF PACEMAKER AND PACEMAKER USING THE SAME" filed on Jun. 20, 2012, and application Ser. No. 13/527,820; "PACEMAKER ELECTRODE LEAD AND PACEMAKER USING THE SAME" filed on Jun. 20, 2012, and application Ser. No. 13/527,836; "PACEMAKER ELECTRODE LEAD AND PACEMAKER USING THE SAME" filed on Jun. 20, 2012, and application Ser. No. 13/527,849.

BACKGROUND

1. Technical Field

The present disclosure relates to an electrode lead of a pacemaker and a pacemaker using the same.

2. Description of Related Art

A pacemaker is an electronic therapeutic device that can be implanted in living beings such as humans. The pacemaker includes a pulse generator and an electrode lead. The pulse generator is used to emit a pulsing current via the electrode lead to stimulate a diseased organ such as a human heart to work normally.

The electrode lead usually includes a lead wire made from metal or alloy. However, a mechanical strength and toughness of the lead wire decreases with the diameter. The fierce seizure suffered by a patient or normal activities of the patient may cause damage to the implanted electrode lead, or the electrode lead may even be broken. Therefore, a working life of the electrode lead of the pacemaker will decrease, threatening the safety of the patient.

What is needed, therefore, is to provide an electrode lead of a pacemaker which has good mechanical strength and toughness, notwithstanding small physical size, to improve the working life of the electrode lead and the pacemaker.

BRIEF DESCRIPTION OF THE DRAWING

Many aspects of the present disclosure can be better understood with reference to the following drawings. The components in the drawings are not necessarily to scale, the emphasis instead being placed upon clearly illustrating the principles of the present embodiments.

DETAILED DESCRIPTION

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean at least one.

Figure 1:
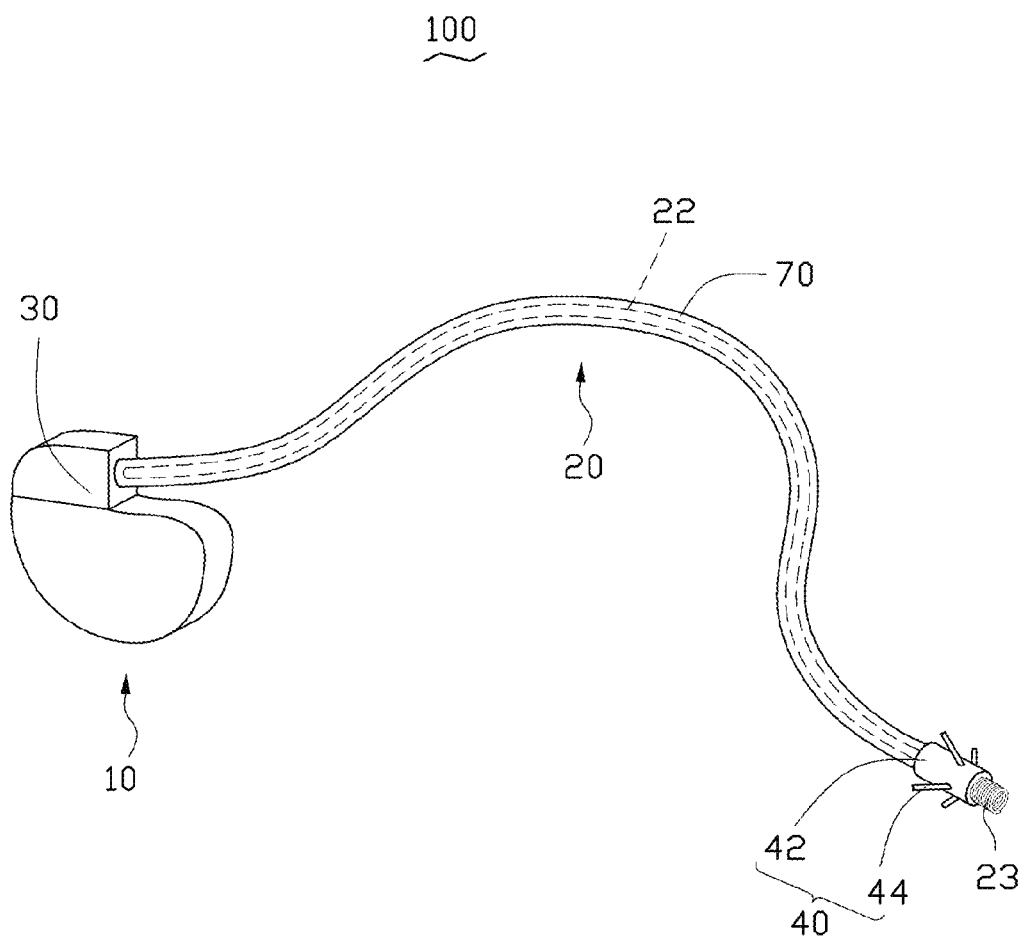
FIG. 1 is an isometric view of one embodiment of a pacemaker.

FIG. 1 shows one embodiment of a pacemaker 100 including a pulse generator 10 and an electrode lead 20 electrically connected with the pulse generator 10. The pulse generator 10 can be used to generate pulse signals to stimulate organs of living beings via the electrode lead 20.

The pulse generator 10 can include a shell (not labeled), a power source (not shown), an output circuit (not shown), a sense circuit (not shown), a control circuit (not shown) and a connector (not shown). The power source, the output circuit, the sense circuit, and the control circuit are packaged in the shell. A material of the shell can be a biocompatible, corrosion resistant, and deformation resistant metal or alloy. In one embodiment, the material of the shell is titanium (Ti). The power source can provide power for the output circuit, the sense circuit, and the control circuit. Chemical batteries such as lithium ion batteries can be used in the power source. In one embodiment, the power source includes a lithium-iodine battery. The control circuit is electrically connected with the output circuit and the sense circuit. The control circuit can control the output circuit and the sense circuit. The output circuit can be used to generate the pulse signals. The sense circuit can be used to receive electrical signals generated by the stimulated organs and feed these electrical signals back to the control circuit. The control circuit can adaptively adjust the output signals of the output circuit according to the feedback of the sense circuit. The connector can be electrically connected with the electrode lead 20. The pulse signals generated by the pulse generator 10 can be transferred to the organ to stimulate the cells. The organs can be a heart, brain, or stomach of living beings.

Figure 2:
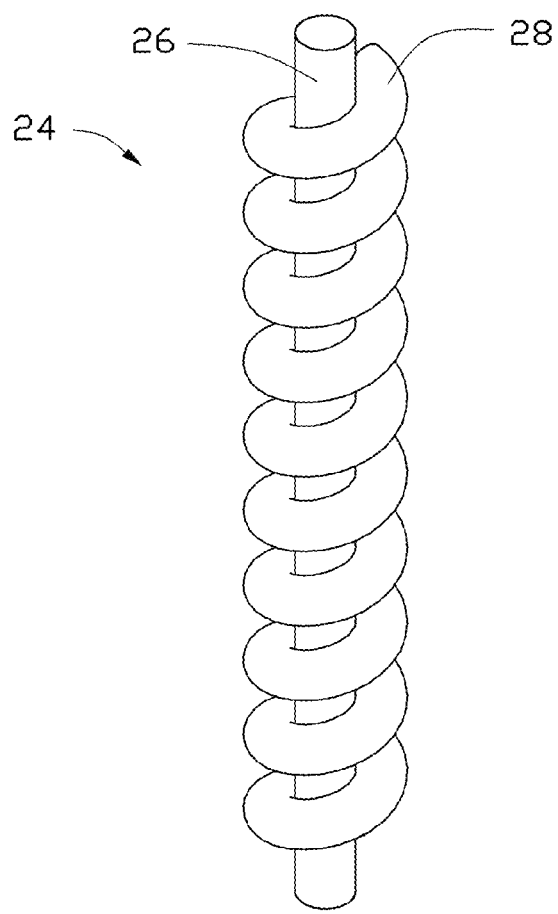
FIG. 2 is a schematic view of an embodiment of a sub-lead wire of the pacemaker.

FIG. 1 and FIG. 2, show the electrode lead 20 can include a lead wire 22 and an electrode head 23 electrically connected with the lead wire 22. The lead wire 22 includes at least one sub-lead wire 24. The sub-lead wire 24 includes a core wire structure 26 and a carbon nanotube composite structure 28 wound around the core wire structure 26.

The electrode lead 20 can further include a connecting element 30 and a fastening element 40. The connecting element 30 and the fastening element 40 are respectively disposed on two opposite ends of the lead wire 22 of the electrode lead 20.

The lead wire 22 can be electrically connected with the connector of the pulse generator 10 by the connecting element 30, thereby connecting with the output circuit and the sense circuit. The connecting element 30 can be a hollow cylindrical structure having an external thread. The connecting element 30 is electrically connected with the connector of the pulse generator 10 by the external thread. A material of the connecting element 30 can be a biocompatible, corrosion resistant, and conductive material, such as platinum or platinum-iridium alloy.

The fastening element 40 is fastened on an end of the lead wire 22 having an electrode head 23. The fastening element 40 can be inserted into the human body. The electrode lead 20 is fastened at a predetermined position of the organ, to prevent the electrode lead 20 from slipping. The electrode head 23 is spaced from the fastening element 40. In one embodiment, the fastening element 40 includes a fastening ring 42 and a plurality of fastening wings 44. The fastening ring 42 can be a cylindrical structure. The fastening wing 44 can be a claviform structure extending along a direction away from the central axis of the fastening ring 42. An angle between an axis of the claviform structure and the central axis of the fastening ring 42 can be in a range from about 30 degrees to about 60 degrees. The fastening wings 44 extend away from the lead wire 22, thereby forming a barb structure. The fastening wings 44 can be wrapped with human tissue after being implanted into the human body to fix the electrode lead 20. The fastening element 40 can be made of a biocompatible macromolecule material, such as polyurethane or silicon rubber.

Figure 3:
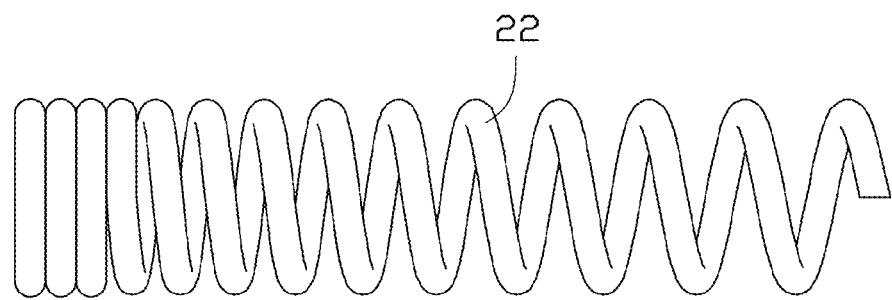
FIG. 3 is a schematic view of an embodiment of a lead wire having a helical structure.
Figure 4:
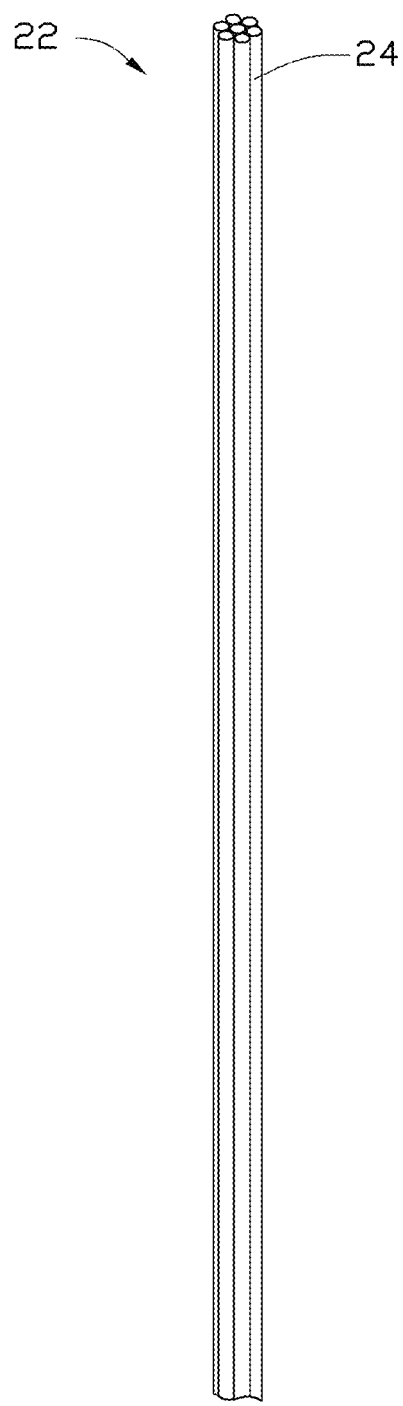
FIG. 4 is a schematic view of an embodiment of a bundle structure composed of a plurality of sub-lead wires compactly arranged in parallel.
Figure 5:
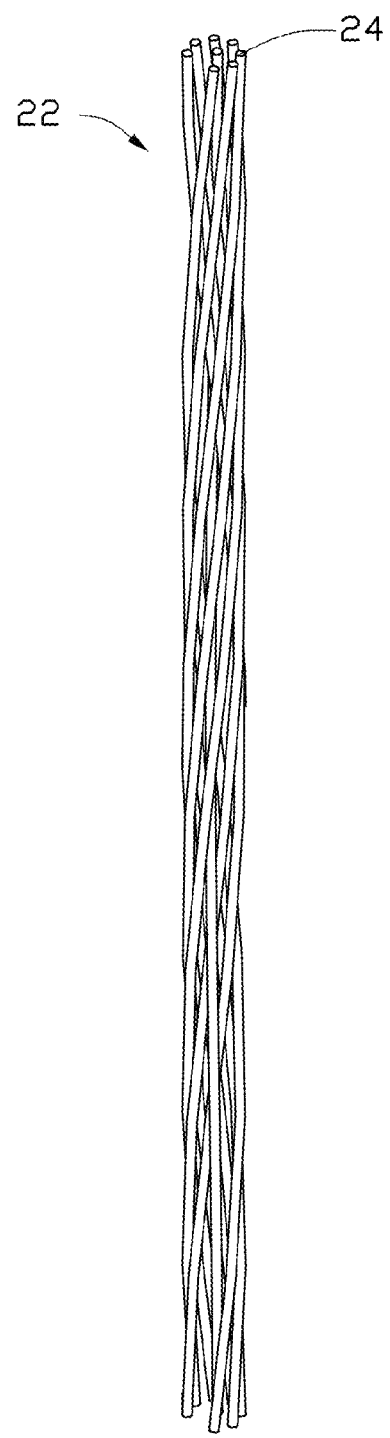
FIG. 5 is a schematic view of an embodiment of a twisted wire structure composed of a plurality of sub-lead wires twisted with each other.

A diameter of the lead wire 22 can be in a range from about 4 millimeters (mm) to about 6 mm. The lead wire 22 can be a linear structure or a helical tubular structure formed by bending the lead wire 22 into a helical shape. FIG. 3 shows the lead wire 22 in a helical tubular structure, which has an excellent elasticity, thereby improving a useful life of the electrode lead 20. The lead wire 22 includes a proximal end and a distal end along an extending direction of the lead wire 22, a screw pitch is increased gradually from the proximal end to the distal end. FIG. 4 shows the lead wire 22 can be a bundle structure composed of a plurality of sub-lead wires 24 substantially parallel to each other. In another embodiment, the lead wire 22 as shown in FIG. 5, can be a twisted wire structure formed by twisting the plurality of sub-lead wires 24 with each other.

The core wire structure 26 of the sub-lead wire 24 can be made of a material having excellent conductivity, high strength, and toughness, such as stainless steel, carbon fiber, tantalum, Ti, zirconium (Zr), niobium (Nb), titanium alloy, copper (Cu), silver (Ag), platinum (Pt), platinum-yttrium alloy, or platinum-palladium alloy. In one embodiment, the material of the core wire structure 26 is Pt.

The carbon nanotube composite structure 28 is wound on an outer surface of the core wire structure 26. In one embodiment, the carbon nanotube composite structure 28 is spirally wound on the outer surface of the core wire structure 26. A screw pitch of the spirally wound carbon nanotube composite structure 28 can be in a range from about 0 mm to about 5 mm. In one embodiment, the screw pitch of the spirally wound carbon nanotube composite structure 28 is about 3 mm. The carbon nanotube composite structure 28 includes a carbon nanotube structure composed of a plurality of carbon nanotubes and a metal material layer combined with the carbon nanotube structure. The metal material layer can be coated on a surface of the carbon nanotube structure or a surface of each of the plurality of carbon nanotubes in the carbon nanotube structure. The carbon nanotube structure can include at least one carbon nanotube wire, at least one carbon nanotube film, or any combination thereof. The carbon nanotube wire can be spirally wound on the outer surface of the core wire structure 26. The carbon nanotube film can be spirally wound on the outer surface of the core wire structure 26. The carbon nanotube film can also be wrapped on the outer surface of the core wire structure 26, and an extending direction of the carbon nanotubes in the carbon nanotube film can be substantially parallel to an axis direction of the lead wire 22.

The carbon nanotube film can be formed by drawing a carbon nanotube segment from a carbon nanotube array. The carbon nanotube segment includes a plurality of carbon nanotubes substantially parallel to each other. The carbon nanotube film includes a plurality of carbon nanotubes that can be arranged substantially parallel to a surface of the carbon nanotube film. A large number of the carbon nanotubes in the carbon nanotube film can be oriented along a preferred orientation, meaning that a large number of the carbon nanotubes in the carbon nanotube film are arranged substantially along a same direction. In the carbon nanotube film, an end of one carbon nanotube is joined to another end of an adjacent carbon nanotube arranged substantially along the same direction by van der Waals attractive force. A small number of the carbon nanotubes are randomly arranged in the carbon nanotube film, and has a small if not negligible effect on the larger number of the carbon nanotubes in the carbon nanotube film arranged substantially along the same direction.

In the carbon nanotube composite structure 28, the plurality of carbon nanotube wires can be arranged in parallel to form a bundle structure, or twisted with each other to form a stranded wire structure.

The carbon nanotube wire can be a non-twisted carbon nanotube wire, a twisted carbon nanotube wire, or any combination thereof.

Figure 6:
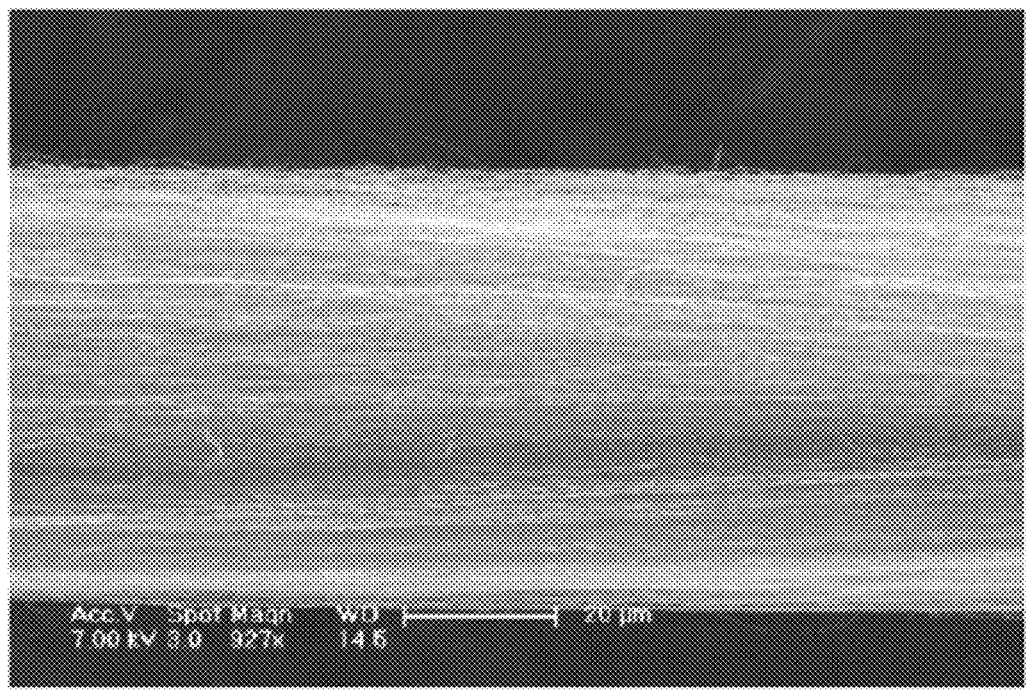
FIG. 6 shows a Scanning Electron Microscope (SEM) image of a non-twisted carbon nanotube wire.

A structure of the non-twisted carbon nanotube wire can be the same as the structure of the above carbon nanotube film having a small width. FIG. 6 shows the non-twisted carbon nanotube wire is a free-standing or stiff structure consisting of a plurality of carbon nanotubes. A majority of the plurality of carbon nanotubes extend in substantially the same direction and parallel to each other. In addition, the majority of the carbon nanotubes are joined end to end by van der Waals attractive forces. Each carbon nanotube in the majority of the carbon nanotubes is joined with the adjacent carbon nanotube lengthwise by van der Waals attractive forces. A minority of the plurality of carbon nanotubes has a random orientation in the non-twisted carbon nanotube wire, and has a very small or negligible effect on the majority of the plurality of carbon nanotubes in view of the arrangement. The non-twisted carbon nanotube wire includes a plurality of successive and preferred-orientation carbon nanotube segments. The plurality of carbon nanotube segments are joined end to end by van der Waals attractive forces. Each of the carbon nanotube segments includes a plurality of carbon nanotubes parallel with each other. The carbon nanotubes in parallel are joined side by side by van der Waals attractive forces. The free-standing or stiff structure of the non-twisted carbon nanotube wire is a result of van der Waals attractive forces acting on the carbon nanotubes joined end to end and side by side. A diameter of the non-twisted carbon nanotube wire can be in a range from about 0.5 nanometers to about 100 microns.

The non-twisted carbon nanotube wire can be formed by the steps of: S(a), choosing a carbon nanotube segment having a predetermined width from a carbon nanotube array by a drawing tool; S(b), moving the drawing tool to pull the chosen carbon nanotube segment at a predetermined speed, thereby pulling out a continuous carbon nanotube wire including the plurality of carbon nanotube segments joined end-to-end by van der Waals attractive forces. Examples of the non-twisted carbon nanotube wire are taught by US Patent US007704480 to Jiang et al.

Figure 7:
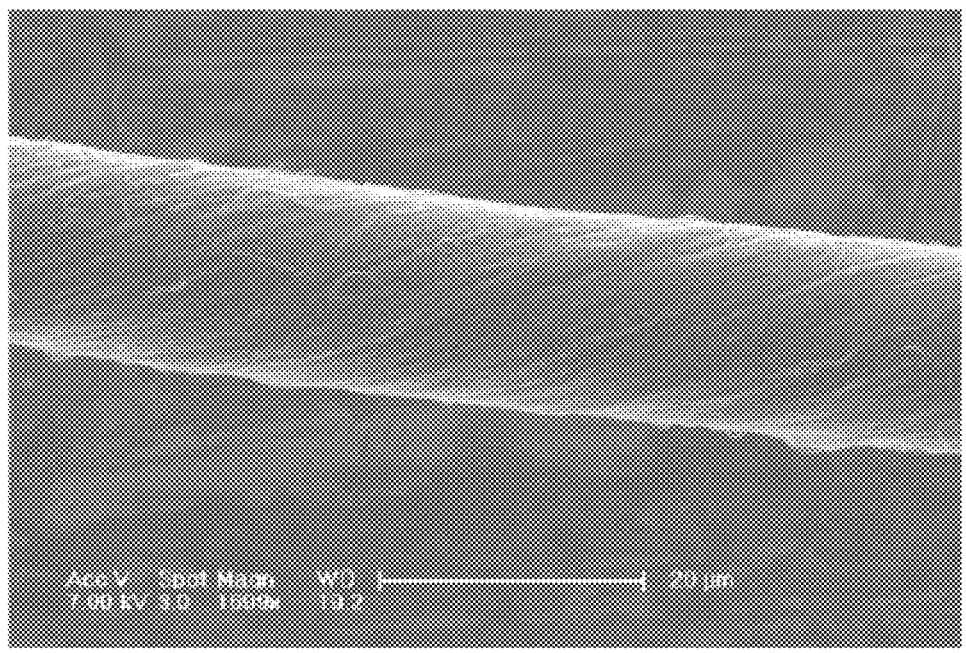
FIG. 7 shows a SEM image of a twisted carbon nanotube wire.

FIG. 7 shows twisted carbon nanotube wire formed by twisting the non-twisted carbon nanotube wire using a mechanical force to turn the two ends of the non-twisted carbon nanotube wire in opposite directions. The twisted carbon nanotube wire includes a plurality of carbon nanotubes oriented around the central axis of the twisted carbon nanotube wire. The carbon nanotubes are aligned helically around the central axis of the twisted carbon nanotube yarn.

The non-twisted carbon nanotube wire and the twisted carbon nanotube wire can be treated with a volatile organic solvent. After being soaked with the organic solvent, the carbon nanotubes adjacent and substantially parallel to each other in the non-twisted or twisted carbon nanotube wire will bundle together due to the surface tension of the organic solvent when the organic solvent volatilizes. A specific surface area and a viscosity of the carbon nanotube wire will decrease, and a density and strength of the carbon nanotube wire will be increased. A tensile strength of the twisted carbon nanotube wire can be greater than 1200 Mega Pascals (MPa). The tensile strength can reach 1.5 Giga Pascals (GPa) if the diameter of the twisted carbon nanotube wire decreases to 10 microns. The volatile organic solvent can be ethanol, methanol, acetone, dichloroethane, chloroform, and any combination thereof. In one embodiment, the volatile organic solvent is ethanol.

The carbon nanotube film and the carbon nanotube wire can be a pure carbon nanotube structure. The pure carbon nanotube structure consists of pristine carbon nanotubes. The characterization "pristine" signifies that the carbon nanotubes are unfunctionalized or not chemically modified.

The carbon nanotube film, the non-twisted carbon nanotube wire and the twisted carbon nanotube wire have a free-standing structure. The term "free-standing structure" can be defined as a structure that does not have to be supported by a substrate. For example, a free-standing structure can sustain the weight of itself when it is hoisted by a portion thereof without any significant damage to its structural integrity. So, if the carbon nanotube film, the non-twisted carbon nanotube wire or the twisted carbon nanotube wire is placed between two separate supporters, a portion of the carbon nanotube film, the non-twisted carbon nanotube wire or the twisted carbon nanotube wire not in contact with the two supporters, would be suspended between the two supporters and yet maintain film structural integrity. The free-standing structure of the carbon nanotube film, the non-twisted carbon nanotube wire or the twisted carbon nanotube wire is realized by the successive carbon nanotubes joined end to end by Van der Waals attractive force.

Figure 8:
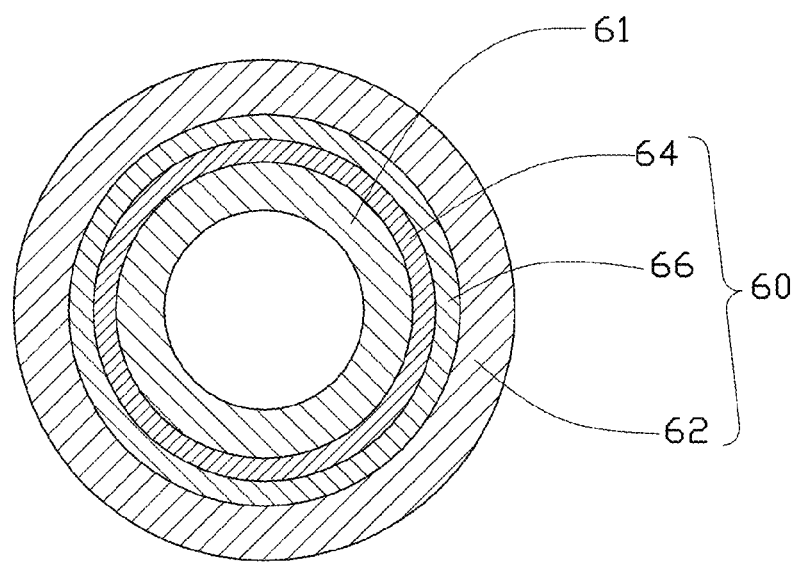
FIG. 8 is a schematic view of a carbon nanotube coated with a metal material layer.
Figure 9:
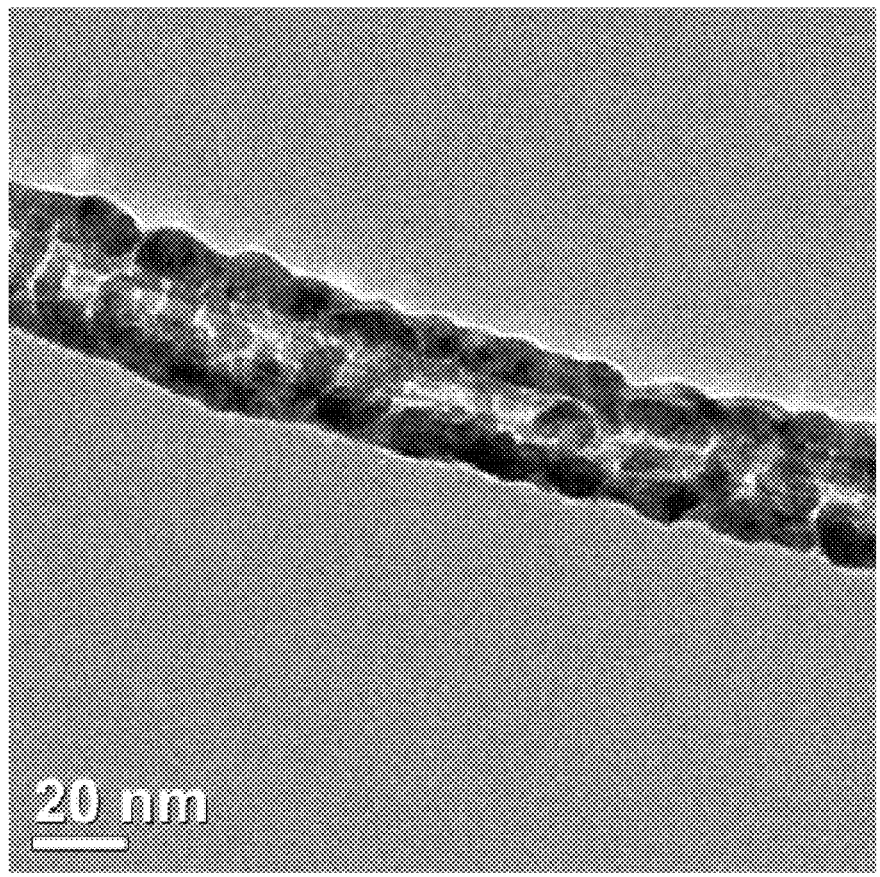
FIG. 9 is a transmission electron microscope (TEM) image of the carbon nanotube coated with the metal material layer.
Figure 10:
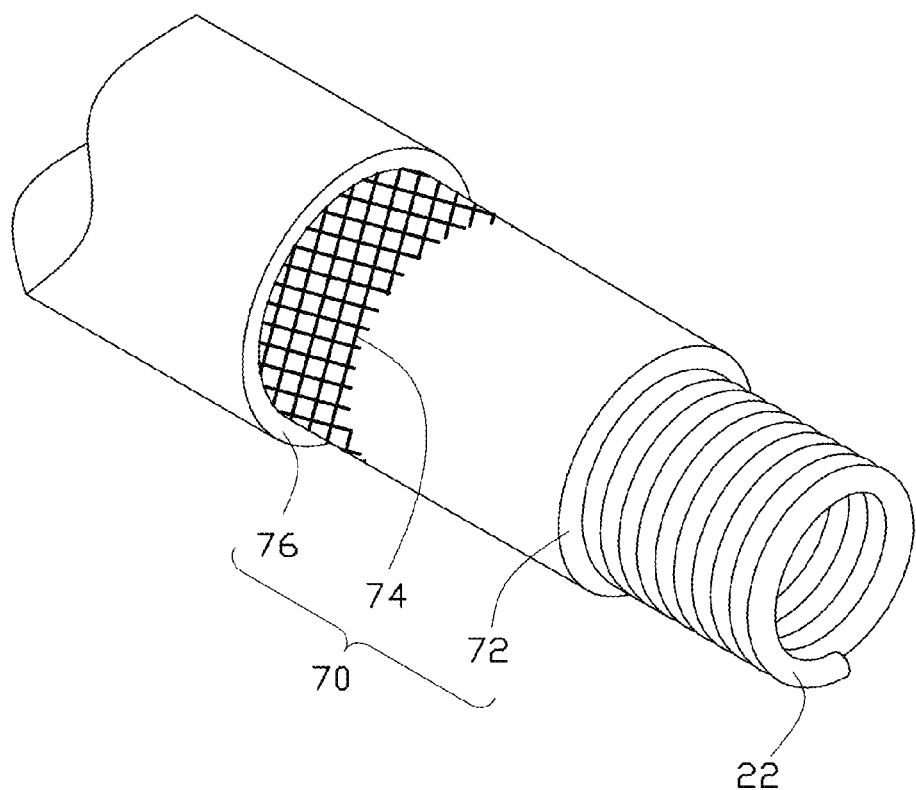
FIG. 10 is a sectional view of an embodiment of an electrode lead.

The metal material layer 60 can be coated on the outer surface of the carbon nanotube structure, or the surface of each of the carbon nanotubes of the carbon nanotube structure. In one embodiment, the metal material layer 60 is coated on the surface of each of the carbon nanotubes of the carbon nanotube wire. FIGS. 8 and 9, show the metal material layer 60 can include a wetting layer 64, a transition layer 66 and a conductive layer 62 successively covering on the surface of the carbon nanotube 61. Specifically, the wetting layer 64 covers the circumferential surface of the carbon nanotube 61, the transition layer 66 covers the outer surface of the wetting layer 64, the conductive layer 62 covers the outer surface of the transition layer 66.

The conductive layer 62 is arranged for enhancing the conductivity of the carbon nanotube composite structure 28. A material of the conductive layer 62 can be at least one of Cu, Ag, gold (Au), or alloys thereof. A thickness of the conductive layer 62 can be in a range from about 1 nm to about 20 nm. In one embodiment, the material of the conductive layer 62 is Au and the thickness is about 2 nm. The carbon nanotube cannot be adequately wetted with most metallic materials, thus, the wetting layer 64 is arranged for wetting the carbon nanotube 61, as well as combining the carbon nanotube 61 with the conductive layer 62. A material of the wetting layer 64 can be at least one of iron (Fe), cobalt (Co), nickel (Ni), palladium (Pd), Ti, and alloys thereof. A thickness of the wetting layer 64 can be in a range from about 1 nm to about 10 nm. In one embodiment, the material of the wetting layer 64 is Ni and the thickness is about 2 nanometers. The transition layer 66 is arranged for combining the wetting layer 64 with the conductive layer 62. A material of the transition layer 66 can be combined with both the material of the wetting layer 64 and the material of the conductive layer 62, such as Cu, Ag, or alloys thereof. A thickness of the transition layer 66 can be in a range from about 1 nm to about 10 nm. In one embodiment, the material of the transition layer 66 is Cu and the thickness is about 2 nm. The transition layer 66 and the wetting layer 64 are optional. If the metal material layer 60 only includes the conductive layer 62, the conductive layer 62 can directly cover the surface of the carbon nanotube 61.

The conductive layer 62, the wetting layer 64 and the transition layer 66 can be formed by a physical method or a chemical method. The physical method can be a physical vapor deposition method such as a vacuum evaporation method or an ion sputtering method. The chemical method can be an electroplating method or a chemical plating method. In one embodiment, the metal material layer 60 is combined with the non-twisted carbon nanotube wire by vacuum evaporation method. In the method, a metal material is vaporized or sublimed to form a metal gas. The metal gas meets the cold carbon nanotube wire and coagulates on the whole circumferential surface of the carbon nanotube wire. The carbon nanotube wire has gaps defined between the carbon nanotubes, and the carbon nanotube wire can be suspended due to the free-standing structure. Thus, the metal material can be permeated into the gaps between the carbon nanotubes, thereby depositing on the whole circumferential surface of each of the carbon nanotubes of the carbon nanotube wire. The metal material layers 60 coated on different carbon nanotubes can also define gaps therebetween.

An adhesive layer can be disposed between the core wire structure 26 and the carbon nanotube composite structure 28. The core wire structure 26 and the carbon nanotube composite structure 28 can be stably adhered together by the adhesive layer. A material of the adhesive layer is not limited. In one embodiment, the material of the adhesive layer is medical adhesive.

The mechanical strength and the toughness of the lead wire 22 can be increased by the wound carbon nanotube composite structure 28 on the outer surface of the core wire structure 26. More specifically, if the lead wire 22 is stretched by a drawing force, the core wire structure 26 will be elongated along the stretching direction. The carbon nanotube composite structure 28 being wound, can prevent the core wire structure 26 from breaking due to a friction force between the carbon nanotube composite structure 28 and the core wire structure 26. In addition, the carbon nanotubes in the carbon nanotube composite structure 28 has excellent mechanical strength, toughness, and conductivity, and the metal material layer 60 can further improve the conductivity of the carbon nanotube composite structure 28. The carbon nanotube composite structure 28 may not be broken with the core wire structure 26, because of the good mechanical strength. The pulse signals can still be transmitted through the carbon nanotube composite structure 28 to the organ. The stimulating and sensing process also can be accomplished by the carbon nanotube composite structure 28. Therefore, the pacemaker can still work. Therefore, a working life of the pacemaker can be prolonged.

The electrode head 23 is electrically connected with the lead wire 22 and can act as a contact end to directly contact and stimulate the organ of the human body. Specifically, the lead wire 22 can transfer the pulse signals to the organ of the human body by the electrode head 23. The electrode head 23 can be used as a stimulating electrode or a sensing electrode.

The electrode head 23 can be a common electrode head used in the pacemaker. The electrode head 23 can be fixed to the lead wire 22 by conductive adhesive or welding. A material of the electrode head 23 can be metal or alloy having an excellent conductivity, such as platinum-iridium alloy. A porous material to ensure biocompatibility can be coated on an outer surface of the electrode head 23. In addition, the porous material can increase the contact area between the electrode head 23 and the human body, thereby increasing the sensitivity and sensing efficiency of the pacemaker. The porous material can be activated carbon, carbon fiber, carbon nanotubes, or titanium-nitrogen alloy.

In one embodiment, the electrode head 23 is integrated with the lead wire 22. A naked end of the lead wire 22 away from the pulse generator 10 can be used as the electrode head 23. Under this situation, there will be no need for an additional electrode head 23 disposed on one end of the lead wire 22. In one embodiment, the distal end of the sub-lead wire 24 of the lead wire 22 is used as the electrode head 23. If the lead wire 22 includes a plurality of sub-lead wires 24, the distal ends of the plurality of sub-lead wires 24 or a portion of the plurality of sub-lead wires 24 can be used as the electrode head 23. A length of the electrode head 23 can be in a range from about 0.5 mm to about 2 mm.

In this embodiment, if the lead wire 22 includes one sub-lead wire 24, the distal end having a linear shape or spiral shape of the sub-lead wire 24 can be used as the electrode head 23. If the lead wire 22 includes a plurality of sub-lead wires 24, the distal ends of the plurality of sub-lead wires 24 can extend along different directions. The electrode head 23 can have a radial shape. The distal ends of the plurality of sub-lead wires 24 can be twisted with each other or be substantially parallel to each other. The electrode head 23 can have a linear shape. Furthermore, the electrode head 23 having a linear shape composed of the distal ends of the plurality of sub-lead wires 24 can be further bent to form a spiral shape.

FIG. 9 shows the electrode lead 20 further including a covering layer 70. The covering layer 70 can include a first insulating layer 72, a shielding layer 74, and a second insulating layer 76.

The first insulating layer 72 can be coated on the surface of the lead wire 22. If the lead wire 22 is spirally bent to form a hollow cylindrical structure, the first insulating layer 72 can be coated on the outer surface of the hollow cylindrical structure. If the lead wire 22 includes the plurality of sub-lead wires 24, the first insulating layer 72 can jointly coat the plurality of sub-lead wires 24, or coat each of the plurality of sub-lead wires 24.

The shielding layer 74 can be coated on an outer surface of the first insulating layer 72. A material of the shielding layer 74 can be a conductive material, such as metal or carbon nanotubes. The shielding layer 74 can be a continuous film structure or a network structure. For example, the shielding layer 74 can be a metal film or a carbon nanotube film. In one embodiment, a metal wire spirally wound on the outer surface of the first insulating layer 72 can be used as the shielding layer 74. The shielding layer 74 can prevent the pulse signal transferred by the lead wire 22 from electromagnetic interference.

The second insulating layer 76 can be coated on an outer surface of the shielding layer 74.

A material of the first insulating layer 72 and the second insulating layer 76 can be the same or different. In this embodiment, the first insulating layer 72 and the second insulating layer 76 can be made of a flexible biocompatible material, such as silicon, polyurethane, polytetrafluoroethylene, or a copolymer of the silicon and polyurethane. A thickness of the first insulating layer 72 and the second insulating layer 76 can be in a range from about 1 micron to about 50 microns.

In one embodiment, an end of the lead wire 22 is used as the electrode head 23 and exposed out from the first insulating layer 72, the shielding layer 74, and the second insulating layer 76.

A working process of the pacemaker 100 acting on the heart of human being is described below. The electrode lead 20 is implanted into the heart of a human, with the electrode head 23 contacting the heart. The pulse signals are generated by the pulse generator 12 and transmitted to the electrode head 23 to stimulate the heart. A heartbeat frequency or a series of heartbeat frequencies can be sensed by detecting potential differences between the electrode head 23 and the pulse generator 12. The potential differences are fed back to the pulse generator 12 to adjust the pulse signals to make the heart beat normally.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. An electrode lead of a pacemaker, the electrode lead comprising:
   a lead wire and an electrode head electrically connected with the lead wire, wherein the lead wire comprises at least one sub-lead wire, and the at least one sub-lead wire comprises a core wire structure and a carbon nanotube composite structure wound around the core wire structure, the carbon nanotube composite structure comprising a plurality of carbon nanotubes joined end to end by van der Waals attractive forces.

2. The electrode lead of claim 1, wherein the carbon nanotube composite structure comprises a carbon nanotube structure and a metal material layer combined with the carbon nanotube structure, the carbon nanotube structure comprising the plurality of carbon nanotubes.

3. The electrode lead of claim 2, wherein the carbon nanotube structure comprises a plurality of carbon nanotube segments joined end to end by van der Waals attractive force, each of the carbon nanotube segments comprises the plurality of carbon nanotubes substantially parallel to each other and joined side by side by van der Waals attractive forces.

4. The electrode lead of claim 2, wherein the carbon nanotube structure is at least one non-twisted carbon nanotube wire, the plurality of carbon nanotubes of the at least one non-twisted carbon nanotube wire extend substantially along one direction.

5. The electrode lead of claim 2, wherein the carbon nanotube structure is at least one twisted carbon nanotube wire, the plurality of carbon nanotubes of the at least one twisted carbon nanotube wire are aligned helically around a central axis of the at least one twisted carbon nanotube wire.

6. The electrode lead of claim 2, wherein the carbon nanotube structure is at least one carbon nanotube film, the plurality of carbon nanotubes of the at least one carbon nanotube film extend substantially along one direction.

7. The electrode lead of claim 6, wherein an extending direction of the plurality of carbon nanotubes in the carbon nanotube composite structure is substantially parallel to an axis direction of the lead wire.

8. The electrode lead of claim 2, wherein the metal material layer coats on a surface of each of the plurality of carbon nanotubes.

9. The electrode lead of claim 8, wherein the metal material layer further comprises a wetting layer and a transition layer successively disposed between the carbon nanotube wire and the conductive layer, and the wetting layer is disposed between the carbon nanotube and the transition layer.

10. The electrode lead of claim 1, wherein the electrode head and the lead wire are integrative, and the electrode head is at a distal end of the lead wire, the lead wire comprises a plurality of sub-lead wires and distal ends of the plurality of sub-lead wires extend along different direction to form a radial shape.

11. The electrode lead of claim 10, further comprises a covering layer covering on an outer surface of the lead wire, and the distal end of the lead wire forms the electrode head exposed out from the covering layer.

12. The electrode lead of claim 11, wherein the covering layer comprises a first insulating layer, a shielding layer, and a second insulating layer successively covering the outer surface of the lead wire.

13. The electrode lead of claim 1, wherein the lead wire is spirally bent into a hollow cylindrical structure.

14. The electrode lead of claim 1, wherein the at least one sub-lead wire is a plurality of sub-lead wires electrically connected with the electrode head, the plurality of sub-lead wires are compactly arranged in parallel to form a bundle structure or twisted with each other to form a twisted wire structure.

15. The electrode lead of claim 1, wherein a material of the core wire structure is a conductive material, and the material of the core wire structure is selected from the group consisting of stainless steel, carbon fiber, tantalum, titanium, zirconium, niobium, titanium alloy, copper, silver, platinum, platinum-yttrium alloy, and platinum-palladium alloy.

16. The electrode lead of claim 1, wherein the lead wire is spirally bent into a hollow cylindrical structure, the lead wire comprises a proximal end and a distal end along an extending direction of the lead wire, a screw pitch is increased gradually from the proximal end to the distal end.

17. A pacemaker comprising:
a pulse generator, and
an electrode lead electrically connected with the pulse generator, the electrode lead comprising a lead wire and an electrode head electrically connected with the lead wire, wherein the lead wire comprises at least one sub-lead wire, and the sub-lead wire comprises a core wire structure and a carbon nanotube composite structure wound around the core wire structure, the carbon nanotube composite structure comprising a plurality of carbon nanotubes joined end to end by van der Waals attractive forces.

* * * * *